United States Patent
Sands

[11] Patent Number: 5,840,723
[45] Date of Patent: Nov. 24, 1998

[54] QUINOXALINE DERIVATIVES FOR TREATING TINNITUS

[75] Inventor: Steven B. Sands, Stonington, Conn.

[73] Assignee: Pfizer Inc., New York, N.Y.

[21] Appl. No.: 728,111

[22] Filed: Oct. 9, 1996

Related U.S. Application Data

[60] Provisional application No. 60/005,217 Oct. 10, 1995.

[51] Int. Cl.⁶ .................................................. A61K 31/495
[52] U.S. Cl. ............................................................. 514/249
[58] Field of Search ............................................. 514/249

[56] References Cited

U.S. PATENT DOCUMENTS 5,563,140  10/1996  Ehrenberger et al. .................. 514/249

*Primary Examiner*—Raymond Henley, III
*Attorney, Agent, or Firm*—Peter C. Richardson; Paul H. Ginsburg; Bryan C. Zielinski

[57] ABSTRACT

A method of treating tinnitus in a mammal in need of such treatment, in which the method comprises administering a therapeutically effective amount of a compound of the formula

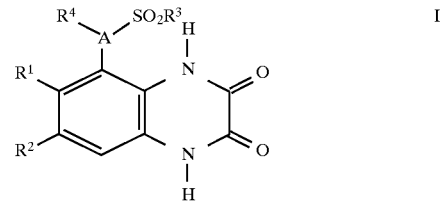

or a pharmaceutically acceptable salt thereof, wherein $R^1$14 $R^4$ are as defined herein.

11 Claims, No Drawings

QUINOXALINE DERIVATIVES FOR TREATING TINNITUS

This application claims domestic priority based on provisional application Ser. No. 60/005,217 filed Oct. 10, 1995.

BACKGROUND OF THE INVENTION

The present invention relates to the treatment of tinnitus using neuroprotective agents defined by formula I below. The compounds of formula I are described in PCT international application number PCT/EP95/03559 (filed Sep. 8, 1995) which designates the United States and which claims priority in United Kingdom patent application number 9419318.2 (filed Sep. 24, 1994). The foregoing PCT international patent application and United Kingdom patent application are incorporated herein by reference in their entirety.

The compounds of formula I antagonize neurotransmission at NMDA receptors. The NMDA receptor is a macromolecular complex consisting of an assembly of protein subunits that possesses distinct binding sites that gate an ion channel permeable to sodium and calcium ions. Hansen and Krogsgaard-Larson, Med. Res. Rev., 10, 55–94 (1990). There are binding sites for glutamic acid, glycine, and polyamines, and a site inside the ion channel where compounds such as phencyclidine (PCP) exert their antagonist effects.

NMDA antagonists are compounds that block the NMDA receptor by interacting with either the glutamate binding site or other sites on the receptor molecule. Examples of NMDA antagonists include D-2 amino 5-phosphonopentanoic acid (D-AP5), and D-2-amino-7-phosphonoheptanoic acid. Schoepp et al., J. Neur. Transm., 85, 131–143 (1991). Antagonists of neurotransmission at NMDA receptors are useful therapeutic agents for the treatment of neurological disorders. J. Lehman, The NMDA Receptor, Drugs of the Future, 14(11), 1059 (1989). U.S. Pat. No. 4,902,695 is directed to a series of competitive NMDA antagonists useful for the treatment of neurological disorders, including epilepsy, stroke, anxiety, cerebral ischemia, muscular spasms, and neurodegenerative disorders such as Alzheimer's disease and Huntington's disease. NMDA antagonists have also been reported to be effective for treating migraine (Canadian J. of Neurological Science, 19(4), 487 (1992)); drug addiction (Science, 251, 85 (1991)); and neuropsychotic disorders related to AIDS (PIPS, 11, 1 (1990)).

The compounds defined by formula I below, and their pharmaceutically acceptable salts, are useful in the treatment of tinnitus by virtue of their selective neuroprotective activity. The neuroprotective activity of the compounds of formula I, and their pharmaceutically acceptable salts, is based on their antiischemic activity and ability to block excitatory amino acid receptors, as described below. The condition known as tinnitus is typically described as a "ringing in the ears". Tinnitus occurs in varying degrees of severity, ranging from minor, sub-clinical annoyance to a severely disabling condition.

Tinnitus is very prevalent among adults. In a survey from Great Britain, about 10% of adults reported having prolonged, spontaneous tinnitus, with 1–3% reporting tinnitus severe enough to be disabling. A. C. Davis, International J. Epidemiology, 18, 911–917 (1989). The incidence in the United States is estimated to be 10–15% of adults having constant tinnitus (up to 35% reporting transient episodes), with 0.1–1% of the population having a severe condition. J. W. P. Hazell (Ed.), Tinnitus, New York: Churchill Livingstone (1987). Severe tinnitus is disabling due to the psychological effect of "hearing" sounds or noise continuously. Tinnitus impairs concentration, disrupts or prevents sleep, and patients suffering with severe symptoms are frequently depressed. M. Sullivan et al., Archives of Internal Medicine, 153, 2251–2259 (1993).

A wide variety of agents have been used in attempts to treat tinnitus including intravenous administration of local anesthetics (lidocaine); trans-tympanic injections of local anesthetics; zinc, steroids, anticonvulsants (carbamazepine), tranquilizers (alprazolam), barbiturates, antidepressants (trimipramine, nortryptyline), and calcium channel blockers (flunarizine). The above listed therapies generally have shown limited efficacy. Although local anesthetics are effective, the route of administration (intravenous or trans-tympanic injection) is not generally acceptable. Alprazolam also has shown some beneficial effect. In a study which germinated in anecdotes from patients receiving alprazolam for other conditions, patients reported that alprazolam (1–1.5 mg/day) provided some relief from symptoms in a 12 week trial, but there was not enough data to determine if alprazolam was acting peripherally to reduce or modify tinnitus in these patients. R. M. Johnson et al., Archives of Otolaryngology, Head and Neck Surgery, 119, 842–845 (1993). Alprazolam, however, carries with it problems associated with chronic use of benzodiazapines (sedation, addiction).

SUMMARY OF THE INVENTION

The present invention is directed to a method of treating tinnitus in a mammal, including a human, in need of such treatment, comprising administering to said mammal a therapeutically effective amount of a compound of the formula

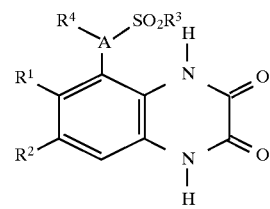

or a pharmaceutically acceptable salt thereof,
wherein:
A represents N or CH;
$R^1$ and $R^2$ are each independently $C_1$–$C_4$ alkyl, halo or $CF_3$;
$R^3$ is $C_3$–$C_7$ cycloalkyl, $CF_3$, $C_6$–$C_{10}$ aryl, or $C_1$–$C_4$ alkyl, wherein said $C_1$–$C_4$ alkyl is optionally substituted by $C_3$–$C_7$ cycloalkyl or $C_6$–$C_{10}$ aryl;
$R^4$ is H, $C_3$–$C_7$ cycloalkyl or $C_1$–$C_6$ alkyl, wherein said $C_1$–$C_6$ alkyl is optionally substituted by hydroxy, $C_1$–$C_4$ alkoxy, $C_6$–$C_{10}$ aryl, $C_3$–$C_9$ heterocyclyl, $C_2$–$C_6$ alkenyl, $C_2$–$C_6$ alkynyl, $C_2$–$C_6$ alkanoyl, $CO_2H$, $C_1$–$C_4$ alkoxycarbonyl, amino, $C_1$–$C_4$ alkylamino, di($C_1$–$C_4$ alkyl)amino, $-NHSO_2CF_3$, $-CONR^5R^6$, $-NHCONR^5R^6$ or $-O(CH_2)_nNR^5R^6$, wherein said $C_6$–$C_{10}$ aryl and said $C_3$–$C_9$ heterocyclyl are optionally substituted by up to 3 substituents independently selected from the group consisting of $C_1$–$C_4$ alkyl, $C_1$–$C_4$ alkoxy, halo and $CF_3$;
$R^5$ and $R^6$ are each independently H or $C_1$–$C_4$ alkyl, or $R^5$ and $R^6$ are taken together to form a pyrrolidino, piperidino or morpholino group; and,
n is 2, 3 or 4.

The term "halo", as used herein, unless otherwise indicated, means fluoro, chloro, bromo or iodo. Preferred halo groups are fluoro, chloro and bromo.

The term "alkyl", as used herein, unless otherwise indicated, includes saturated monovalent hydrocarbon radicals having straight or branched moieties.

The term "alkenyl", as used herein, unless otherwise indicated, includes alkyl groups, as defined above, having a carbon-carbon double bond.

The term "alkynyl", as used herein, unless otherwise indicated, includes alkyl groups, as defined above, having a carbon-carbon triple bond.

The term "alkanoyl", as used herein, unless otherwise indicated, includes alkylcarbonyl groups wherein the alkyl moiety is as defined above.

The term "alkoxy", as used herein, unless otherwise indicated, includes O-alkyl groups wherein the alkyl moiety is as defined above.

The term "cycloalkyl", as used herein, unless otherwise indicated, includes saturated monovalent cyclo hydrocarbon radicals including cyclobutyl, cyclopentyl and cycloheptyl.

The term "aryl", as used herein, unless otherwise indicated, includes an organic radical derived from an aromatic hydrocarbon by removal of one hydrogen, such as phenyl or naphthyl.

The term "heterocyclyl", as used herein, unless otherwise indicated, includes aromatic and non-aromatic heterocyclic groups containing one or more heteroatoms each selected from O, S and N. The heterocyclic groups include benzo-fused ring systems and ring systems substituted with an oxo moiety. With reference to the $R^4$ substituent of formula I, the $C_3$–$C_9$ heterocyclic group can be attached to the $C_1$–$C_6$ alkyl group by a nitrogen or, preferably, a carbon atom. An example of a $C_3$ heterocyclic group is thiazolyl, and an example of a $C_3$ heterocyclic group is quinolinyl. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl and thiazolyl. Heterocyclic groups having a fused benzene ring include benzimidazolyl.

The phrase "treatment of tinnitus" as used herein, unless otherwise indicated, includes methods to cure, lessen or prevent tinnitus, regardless of its cause, in a mammal, such as a human. An example of preventing tinnitus would be the use of the compounds of formula I, or their pharmaceutically acceptable salts, prior to or during the use of certain cancer treatment drugs that are associated with drug-induced ototoxicity.

The phrase "therapeutically effective amount", as used herein, unless otherwise indicated, means an amount effective in the treatment of tinnitus, as defined above.

The phrase "pharmaceutically acceptable salt(s)", as used herein, unless otherwise indicated, includes salts of acidic or basic groups which may be present in the compounds of formula I. For example, pharmaceutically acceptable salts include sodium, calcium and potassium salts of carboxylic acid groups and hydrochloride salts of amino groups. Other pharmaceutically acceptable salts of amino groups are hydrobromide, sulfate, hydrogen sulfate, phosphate, hydrogen phosphate, dihydrogen phosphate, acetate, succinate, citrate, tartrate, lactate, mandelate, methanesulfonate (mesylate) and p-toluenesulfonate (tosylate) salts.

Certain compounds of formula I may have asymmetric centers and therefore exist in different enantiomeric forms. This invention relates to the use of all optical isomers and stereoisomers of the compounds of formula I and mixtures thereof. The compounds of formula I may also exist as tautomers. This invention relates to the use of all such tautomers and mixtures thereof.

Certain compounds of formula I in which an O or N atom in $R^4$ is connected to A vial single carbon atom may not be sufficiently stable to be used in the method of the present invention. It is understood that any such unstable compounds do not form part of the present invention.

In the method of the invention, preferred compounds of formula I include those in which $R^1$ and $R^2$ are independently selected from halo and $C_1$–$C_4$ alkyl.

Other preferred methods include the use of the compounds of formula I in which $R^3$ is $C_1$–$C_4$ alkyl, or, more preferably, methyl.

Other preferred methods include the use of the compounds of formula I in which $R^4$ is $C_1$–$C_6$ alkyl substituted by hydroxy or $CO_2H$. More preferably, $R^4$ is $CH_2CH_2OH$ or $CH_2CO_2H$.

Other preferred methods include the use of the compounds of formula I in which A is N.

Rotation about the bond between A and the 1,4-dihydro-2,3-dioxoquinoxaline ring may be restricted, and so atropisomerism may arise. Preferably, when A represents N, the compounds of formula I have the stereochemical orientation of formula IA below:

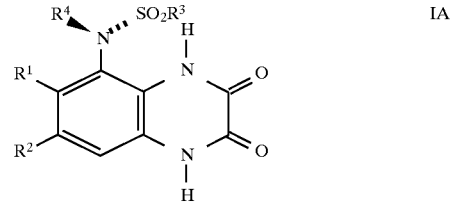

IA

Preferred compounds of formula I for use in the method of the invention include
(R)-N-(1,4-dihydro-6,7-dichloro-2,3-dioxoquinoxalin-5-yl)-N-(2-hydroxyethyl)methane-sulphonamide and
(R)-N-(carboxyethyl)-N-(1,4-dihydro-6,7-dichloro-2,3-dioxoquinoxalin-5-yl)methane-sulphonamide.

DETAILED DESCRIPTION OF THE INVENTION

The compounds of formula I are readily prepared. In particular, the compounds of formula I can be prepared by one or more of the synthetic methods referred to in PCT international application number PCT/EP95/03559 and United Kingdom patent application number 9419318.2, referred to above.

As described in PCT international application number PCT/EP95/03559, referred to above, the compounds of formula I can be prepared by removing the protecting groups from a compound of the formula

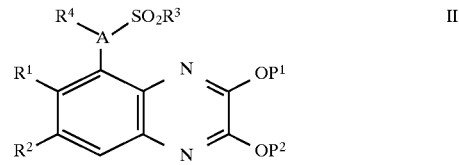

II wherein A and $R^1$–$R^4$ are as defined above, and $P^1$ and $P^2$ are protecting groups. Appropriate protecting groups which $P^1$ and $P^2$ represent include benzyl and $C_1$–$C_6$ alkyl, in particular methyl. These protecting groups can be removed using conventional deprotection methods (see T. W. Greene and P. G. M. Wuts, *Protective Groups in Organic Synthesis*, John Wiley and Sons Inc, 1991). For example, when $P^1$ or $P^2$ is methyl, the protecting group can be removed by acidic hydrolysis using dilute aqueous hydrochloric acid (e.g. 2 molar). The reaction is typically carried out by heating the compound of formula I, preferably under reflux, in a mixture of dilute aqueous hydrochloric acid and a suitable organic solvent such as dioxane or acetone for 2 to 48 hours until reaction is complete. The resulting compound of formula I can then be isolated and purified by conventional procedures.

Compounds of formula II in which $R^4$ is other than hydrogen can be prepared by reaction of a corresponding compound of formula II in which $R^4$ is H with the appropriate halide of formula $R^{4a}X$, wherein X is Cl, Br or I and $R^{4a}$ is defined as $R^4$ is defined above with the proviso that $R^{4a}$ cannot be H. The reaction is done in the presence of a base such as potassium t-butoxide. Typically the base is added to a solution of the compound of formula II (wherein $R^4$ is H) in a suitable organic solvent such as dimethylformamide. After stirring for a few minutes, the halide $R^{4a}X$ is added and the mixture is stirred for a few hours at room temperature. The desired intermediate can then be isolated and purified by conventional procedures.

In addition, compounds of formula II can be prepared using conventional synthetic methods. For example, compounds in which A is CH, and $R^4$ is allyl can be converted to compounds in which $R^4$ is 2-hydroxyethyl by ozonolysis followed by reduction. Compounds of formula II in which A is CH, and $R^4$ is allyl can be prepared from corresponding compounds of formula II in which $R^4$ is H by reaction with diallyl carbonate.

As an alternative to the above alkylation procedure when A is N, the Mitsunobu reaction can be used. This involves the reaction of an alcohol of the formula $R^{4a}OH$ (in which $R^{4a}$ is as defined above) with diethyl azodicarboxylate, triphenylphosphine and a compound of formula II in which $R^4$ is H. The reaction is typically carried out in a suitable organic solvent, e.g. tetrahydrofuran, at room temperature with stirring for 6 to 12 hours.

Compounds of formula II in which $R^4$ is a $C_1$–$C_6$ alkyl group substituted by hydroxy can also be prepared by the methods of Preparations 8 to 10 in PCT international application number PCT/EP95/03559, referred to above, which involve the formation of an alkanoylalkyl derivative which is either reduced with a hydride reducing agent, such as diisobutylaluminium hydride, or reacted with an alkylmagnesium halide.

Compounds of formula II in which $R^4$ is hydrogen and A is N can be prepared by sulphonylation of a corresponding quinoxaline of the formula

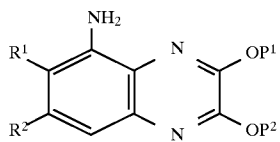

wherein $R^1$, $R^2$, $P^1$ and $P^2$ are as defined above, using an appropriate sulphonyl chloride of formula $R^3SO_2Cl$ or anhydride of formula $(R^3SO_2)_2O$, in which $R^3$ is as defined above, in a suitable organic solvent, such as dichloromethane or tetrahydrofuran, in the presence of an acid acceptor such as pyridine or triethylamine. In certain cases, if a large excess of the sulphonyl chloride or anhydride is used, then a degree of di-sulphonylation may occur. In this situation, one of the $R^3SO_2$— substituents can be removed by reaction of the di-sulphonylated product with aqueous sodium hydroxide. Compounds of formula III can be prepared by conventional techniques such as those illustrated in Preparations 1 and 2 of PCT international application number PCT/EP95/03559, referred to above.

Compounds of formula II in which $R^4$ is hydrogen and A is CH can be prepared by reaction of a compound of formula

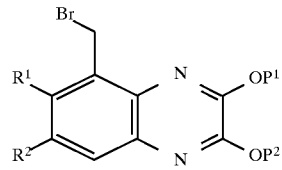

in which $R^1$, $R^2$, $P^1$ and $P^2$ are as defined above, with a thiolate of formula $NaSR^3$, in which $R^3$ is as defined above, followed by oxidation using a peracid such as 3-chloroperbenzoic acid. Compounds of formula IV can be prepared by conventional synthetic techniques.

In the synthesis of the compounds of formula I it may be necessary or desirable to protect sensitive functional groups and then deprotect them. Methods for such operations are known to those skilled in the art and are described in *Protective Groups in Organic Synthesis,* referred to above.

The pharmaceutically acceptable salts of the compounds of formula I are readily prepared. The compounds of formula I contain at least two amine groups which are basic and capable of forming acid addition salts. In general, such salts are formed by reacting the base forms with the appropriate acid. When the salt is of a monobasic acid (e.g., the hydrochloride, the hydrobromide, the p-toluenesulfonate, the acetate), the hydrogen form of a dibasic acid (e.g., the dihydrogen phosphate, the citrate), at least one molar equivalent and usually a molar excess of the acid is employed. However, when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent. The compounds of formula I may also contain a carboxylic acid group and therefore be capable of forming cationic salts. Such salts are generally prepared by combining a compound of formula I with one molar equivalent of NaOH or KOH in a suitable solvent.

The compounds of formula I, and their pharmaceutically acceptable salts, possess selective neuroprotective activity based upon their antiischemic activity and ability to block excitatory amino acid receptors. The preferred procedure for evaluating the neuroprotective activity of this compound is that described by Ismail A. Shalaby, et al., in *J. Pharm. and Experimental Therapeutics,* 260, 925 (1992). This article is incorporated herein by reference in its entirety and is described below.

Cell culture.

Seventeen day fetal rat (CD, Charles River Breeding Laboratories, Inc., Wilmington, Mass.) hippocampal cells are cultured on PRIMARIA culture plates (Falcon Co., Lincoln Park, N.J.) for 2 to 3 weeks in serum containing culture medium (minimum essential medium with nonessential amino acids, containing 2 mM glutamine, 21 mM glucose, penicillin/streptomycin (5000 U each), 10% fetal bovine serum (days 1–7) and 10% horse serum (days 1–21). Cells are either plated on 96-well microtiter plates at a density of 80,000 cells per well or on 24-well culture plates at a density of 250,000 cells per well. Cultures are grown at 37° C. in a humidified $CO_2$ tissue culture incubator containing 5% $CO_2$-95% air. Proliferation of nonneuronal cells is controlled by adding 20 μM uridine and 20 μM 5fluoro-2-deoxyuridine (Sigma Chemical Co., St. Louis, Mo.) from days 6 to 8 of culture. Culture media is exchanged every 2 to 3 days with fresh stock.

Glutamate toxicity.

The cultures are assessed for glutamate toxicity 2 to 3 weeks from initial plating. Culture media is removed and cultures rinsed twice with a CSS (in millimolar:): NaCl (12); KCl (5.4); MgCl$_2$ (0.8); CaCl$_2$ (1.8); glucose (15); and 4-(2-hydroxyethyl)-1-piperazineethanesulfonic acid (25) (pH 7.4). Cultures are then exposed for 15 min (37° C.) to various concentrations of glutamate. After this incubation, cultures are rinsed 3 times with glutamate-free CSS and twice with fresh culture medium without serum. The cultures are then incubated for 20 to 24 hr in serum4ree culture medium. The compound being tested is added 2 min before and during the 15-min exposure to glutamate. In some experiments, the compound is added at different times after the glutamate exposure and for the following 20 to 24 hr.

Cell viability is routinely assessed 20 to 24 hours after the excitotoxin exposure by measuring the activity of the cytosolic enzyme LDH. LDH activity is determined from the culture medium of each of the 96 wells of the microtiter plates. A 50-μl sample of the media is added to an equal volume of sodium-phosphate buffer (0.1M, pH 7.4) containing 1.32 mM sodium pyruvate and 2.9 mM NADH. The 340 nm absorbance of the total reaction mixture for each of the 96 wells is monitored every 5 sec for 2 min by an automated spectrophotometric microtiter plate reader (Molecular Devices; Menlo Park, Calif.). The rate of absorbance is automatically calculated using an IBM SOFTmax program (version 1.01; Molecular Devices) and is used as the index of LDH activity.

Morphological assessment of neuronal viability is determined using phrase contrast microscopy. The 96-well culture plates do not permit good phase-contrast imagery, so cells cultured on 24-well plates are used for this purpose. Quantitatively, both culture platings are equally sensitive to glutamate toxicity, and display 2- to 3-fold increases in LDH activity 24 hours after exposure to 0.1 to 1.0 mM glutamate.

Reagents.

DTG can be purchased from Aldrich Chemical Company (Milwaukee, Wis.), and haloperidol from Research Biochemicals Inc. (Natick, Mass.). Spermine can be purchased from Sigma Chemical Co. (St. Louis, Mo.). Horse and fetal bovine serum can be purchased from Hyclone (Logan, Utah). Culture medium, glutamine and penicillin/streptomycin can be purchased from Gibco Co. (Grand Island, N.Y.).

Data analysis.

Neurotoxicity can be quantified by measuring the activity of LDH present in the culture medium 20 to 24 hours after glutamate exposure. The increased LDH activity in the culture media correlates with destruction and degeneration of neurons (Koh and Choi, 1987). Because actual levels of LDH vary from different cultures, data are routinely expressed relative to buffer-treated sister wells of the same culture plate. To obtain an index of LDH activity from glutamate and drug-treated cultures, the LDH values from control cultures are subtracted from that of the treatment groups. Data for drug treatments is expressed as a percentage of the increase in LDH induced by 1 mM glutamate (or NMDA) for each experiment. Concentrations of NMDA antagonists required to reverse 50% of the LDH increase induced by excitotoxins (IC$_{50}$) are calculated using log-probit analysis from the pooled results of three independent experiments.

The neuroprotective activity of the compounds of formula I, and their pharmaceutically acceptable salts, render them useful in the treatment of tinnitus.

In the treatment of tinnitus using a compound of formula I, or a pharmaceutically acceptable salt thereof, the therapeutically-effective oral dosage is typically from about 0.1 to 100 mg/kg body weight of the subject to be treated, preferably from 1 to 10 mg/kg, and an intravenous dosage typically ranges from 0.01 mg/kg to 10 mg/kg, preferably from 0.1 to 5 mg/kg. Where necessary, the dose may be administered by intravenous infusion, at a dosage ranging from 0.01 to 1 mg/kg/hr. Of course, depending upon the exact nature of the illness and the condition of the patient, doses outside this range may be prescribed by the attending physician. The oral route of administration is generally preferred. However, if the patient is unable to swallow, or oral absorption is otherwise impaired, another route of administration such as suppositories, or parenteral (i.m., i.v.) or topical administration will be appropriate.

The compounds of formula I, and their pharmaceutically acceptable salts, can be administered in the form of pharmaceutical compositions together with a pharmaceutically acceptable vehicle or diluent. Such compositions are generally formulated in a conventional manner utilizing solid or liquid vehicles or diluents as appropriate to the mode of desired administration: for oral administration, in the form of tablets, hard or soft gelatin capsules, suspensions, granules, powders and the like; for parenteral administration, in the form of injectable solutions or suspensions, and the like; and for topical administration, in the form of solutions, lotions, ointments, salves and the like.

For purposes of oral administration, tablets containing excipients such as sodium citrate, calcium carbonate and dicalcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as, but not limited to, magnesium stearate, sodium lauryl sulfate and talc are often very useful for tableting purposes. Solid compositions of a similar type may also be employed as fillers in soft elastic and hard-filled gelatin capsules; preferred materials in this connection also include, by way of example and not of limitation, lactose or milk sugar as well as high molecular weight polyethylene glycols. When aqueous suspensions and/or elixirs are desired for oral administration, the essential active ingredient may be combined with various sweetening or flavoring agents, coloring matter or dyes and, if so desired, emulsifying and/or suspending agents, together with diluents such as water, ethanol, propylene glycol, glycerin and various like combinations thereof.

What is claimed is:

1. A method of treating tinnitus in a mammal comprising administering to a mammal in need of such treatment a therapeutically effective amount of a compound of the formula

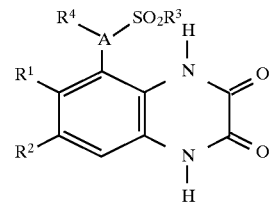

or a pharmaceutically acceptable salt thereof, wherein:

A represents N or CH;

$R^1$ and $R^2$ are each independently $C_1-C_4$ alkyl, halo or $CF_3$;

$R^3$ is $C_3-C_7$ cycloalkyl, $CF_3$, $C_6-C_{10}$ aryl, or $C_1-C_4$ alkyl, wherein said $C_1-C_4$ alkyl is optionally substituted by $C_3-C_7$ cycloalkyl or $C_6-C_{10}$ aryl;

$R^4$ is H, $C_3-C_7$ cycloalkyl or $C_1-C_6$ alkyl, wherein said $C_1-C_6$ alkyl is optionally substituted by hydroxy, $C_1-C_4$ alkoxy, $C_6-C_{10}$ aryl, $C_3-C_6$ heterocyclyl, $C_2-C_6$ alkenyl, $C_2-C_6$ alkynyl, $C_2-C_6$ alkanoyl, $CO_2H$, $C_1-C_4$ alkoxycarbonyl, amino, $C_1-C_4$ alkylamino, di($C_1-C_4$ alkyl)amino, $-NHSO_2CF_3$, $-CONR^5R^6$, $-NHCONR5R^6$ or $-O(CH_2)_nNR^5NR^6$; and said $C_6-C_{10}$ aryl and said $C_3-C_9$ heterocyclyl are optionally substituted by up to 3 substituents independently selected from the group consisting of $C_1-C_4$ alkyl, $C_1-C_4$ alkoxy, halo and $CF_3$;

$R^5$ and $R^6$ are each independently H or $C_1-C_4$ alkyl, or $R^5$ and $R^6$ are taken together to form a pyrrolidino, piperidino or morpholino group; and, n is 2, 3 or 4.

2. The method of claim 1 wherein A is N.

3. The method of claim 1 wherein $R^1$ is halo or $C_1-C_4$ alkyl.

4. The method of claim 1 wherein $R^2$ is halo or $C_1-C_4$ alkyl.

5. The method of claim 1 wherein $R^3$ is $C_1-C_4$ alkyl.

6. The method of claim 5 wherein $R^3$ is methyl.

7. The method of claim 1 wherein $R^4$ is $C_1-C_6$ alkyl substituted by hydroxy or $CO_2H$.

8. The method of claim 7 wherein $R^4$ is $CH_2CH_2OH$ or $CH_2CO_2H$.

9. The method of claim 2 wherein the compound of formula I, or a pharmaceutically acceptable salt thereof, has the stereochemical orientation of formula IA:

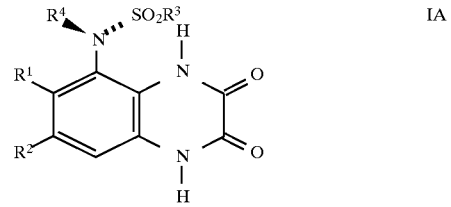

10. The method of claim 1 wherein the compound of formula I is (R)-N-(1,4-dihydro-6,7-dichloro-2,3-dioxoquinoxalin-5-yl)-N-(2-hydroxyethyl)methane-sulphonamide, or a pharmaceutically acceptable salt thereof.

11. The method of claim 1 wherein the compound of formula I is (R)-N-(carboxyethyl)-N-(1,4-dihydro-6,7-dichloro-2,3-dioxoquinoxalin-5-yl)methane-sulphonamide, or a pharmaceutically acceptable salt thereof.

* * * * *